United States Patent [19]
Tomcufcik et al.

[11] 4,283,334

[45] Aug. 11, 1981

[54] 2,3-DISUBSTITUTED-2,3,6,7,8,9-HEXAHYDRO-5H-THIAZOLO[3,2-a]-[1,3]DIAZOCIN-3-OLS

[75] Inventors: Andrew S. Tomcufcik, Old Tappan; William B. Wright, Jr., Woodcliff Lake, both of N.J.; Joseph W. Marsico, Jr., Pearl River, N.Y.

[73] Assignee: American Cyanamid Company, Stamford, Conn.

[21] Appl. No.: 100,673

[22] Filed: Dec. 5, 1979

[51] Int. Cl.$^3$ ............................................ C07D 277/00
[52] U.S. Cl. .................................. 260/245.5; 424/270
[58] Field of Search ...................................... 260/245.5

[56] References Cited

U.S. PATENT DOCUMENTS

| | | | |
|---|---|---|---|
| 3,763,142 | 10/1973 | Manning | 260/245.5 |
| 4,162,253 | 7/1979 | Acheson et al. | 260/245.5 |

FOREIGN PATENT DOCUMENTS 1365977  9/1974  United Kingdom ................ 260/245.5

OTHER PUBLICATIONS

Chem. Abstracts 87:5932n.

*Primary Examiner*—Ethel G. Love
*Attorney, Agent, or Firm*—Edward A. Conroy, Jr.

[57] ABSTRACT

2,3-Disubstituted-2,3,6,7,8,9-hexahydro-5H-thiazolo[3,2-a]-[1,3]diazocin-3-ols which are new compounds useful as diuretic agents.

8 Claims, No Drawings

2,3-DISUBSTITUTED-2,3,6,7,8,9-HEXAHYDRO-5H-THIAZOLO[3,2-a]-[1,3]DIAZOCIN-3-OLS

DESCRIPTION OF THE INVENTION

This invention is concerned with new compounds of the formula:

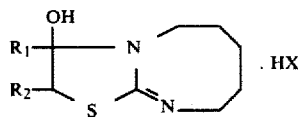

wherein $R_1$ is selected from the group comprising aryl, substituted aryl and a heterocycle; $R_2$ is selected from the group comprising hydrogen, alkyl ($C_1$–$C_4$), aryl, substituted aryl and a heterocycle, as well as the pharmaceutically acceptable salts thereof, wherein the salt forming moiety (X) is selected from the group comprising chloro, bromo and methane sulfonate. Preferred compounds are those wherein $R_1$ is phenyl, p-chlorophenyl, 2,3,4-trichlorophenyl, 2-chloro-5-trifluoromethylphenyl or 2-thienyl; $R_2$ is hydrogen, methyl or phenyl; and X is chloro or bromo.

The novel compounds of the present invention may be prepared in accordance with the following flowchart.

FLOWCHART

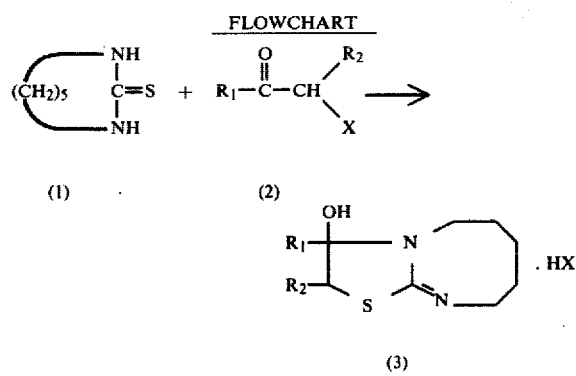

In accordance with the above flowchart hexahydro-1,3-diazocine-2(1H)-thione (1) is dissolved in acetone with heat and then clarified. An acetone solution of the ketone (2) is added and the mixture is stirred for several hours, producing the products (3) where $R_1$, $R_2$ and X are as previously described.

The novel compounds of the present invention are physiologically active and, therefore, useful in the pharmaceutical field. In particular, these compounds are useful as diuretics which greatly enhance the excretion of sodium ions with minimal effect upon the excretion of potassium ions.

The novel compounds of the present invention are potent diuretics, producing significant water diuresis and sodium ($Na^+$) loss, but with minimal loss of potassium ($K^+$), as determined in the following procedure.

One to three spontaneously hypertensive rats are dosed by gavage with a test compound at 100 mg./kg. of body weight and loaded with 0.9% sodium chloride at 25 ml./kg. of body weight at zero hour. The 0–5 hour urine is collected, its volume measured, and $Na^+$ and $K^+$ concentrations determined.

The results of this test on typical compounds of this invention are given in Table I, wherein the sodium and potassium levels are given in terms of milliequivalents (meq.) excreted per 5 hours with a normal sodium control being 0.60 meq. per 5 hours.

TABLE I

| | | Total meq./5 Hours | |
|---|---|---|---|
| Compound | Urine Volume ml./5 Hours | $Na^+$ | $K^+$ |
| 3-(p-Chlorophenyl)-2,3,6,7,8,9-hexahydro-5H-thiazolo[3,2-a]-[1,3]diazocin-3-ol, hydrobromide | 16.0 | 1.58 | 0.53 |
| 2,3,6,7,8,9-Hexahydro-2,3-diphenyl-5H-thiazolo[3,2-a][1,3]diazocin-3-ol, hydrobromide | 12.0 | 1.43 | 0.36 |
| 2,3,6,7,8,9-Hexahydro-3-(2,3,4-trichlorophenyl)-5H-thiazolo-[3,2-a][1,3]diazocin-3-ol, hydrobromide | 14.5 | 1.49 | 0.84 |
| 3-(p-Chlorophenyl)-2,3,6,7,8,9-hexahydro-2-methylthiazolo-[3,2-a][1,3]diazocin-3-ol, hydrobromide | 15.0 | 1.69 | 0.83 |
| 2,3,6,7,8,9-Hexahydro-2-methyl-3-phenyl-5H-thiazolo[3,2-a]-[1,3]diazocin-3-ol, hydrobromide | 21.8 | 2.35 | 2.21 |

The novel compounds of the present invention have thus been shown to be valuable diuretic agents of low toxicity when administered orally. The amount of a single dose or of a daily dose will vary but should be such as to give a proportionate dosage of from about 5 mg. to about 100 mg. per day for a subject of about 70 kg. body weight. The dosage regimen may be adjusted to provide the optimum therapeutic response, for example, doses of 1.0–25 mg. may be administered on a four times per day regimen, or the dose may be proportionately increased as indicated by the exigencies of the therapeutic situation.

The compounds of the present invention may be administered as active components of compositions in unit dosage form such as tablets, pills, capsules, powders, granules, oral solutions or suspensions and the like. For preparing solid compositions such as tablets, the active compound is mixed with conventional tableting ingredients such as starch, lactose, sucrose, sorbitol, talc, stearic acid, magnesium stearate, dicalcium phosphate, gums and functionally similar materials as pharmaceutical diluents or carriers. The tablets or pills can be laminated or otherwise compounded to provide a dosage form affording the advantage of prolonged or delayed action, or predetermined successive action of the enclosed medication. For example, the tablet or pill can comprise an inner dosage and an outer dosage component, the latter being in the form of an envelop over the former. The two components can be separated by an enteric layer which serves to resist disintegration in the stomach and permits the inner component to pass intact into the duodenum or to be delayed in release. A variety of materials can be used for such enteric layers or coatings, such materials including a number of polymeric acids or mixtures of polymeric acids with such materials as shellac, shellac and cetyl alcohol, cellulose acetate, and the like. A particularly advantageous enteric coating comprises a styrene maleic acid copolymer together with known materials contributing to the enteric properties of the coating.

The liquid forms in which the compounds of the present invention may be incorporated for administration include aqueous solutions, suitably flavored syrups, aqueous or oil suspensions, flavored emulsions with edible oils such as cottonseed oil, sesame oil, coconut oil, peanut oil, and the like, as well as elixirs and similar pharmaceutical vehicles. Suitable dispersing or suspending agents for aqueous suspensions include synthetic and natural gums such as tragacanth, acacia, alginic acid, dextran, sodium carboxymethylcellulose, methylcellulose, polyvinylpyrrolidone, gelatin and the like.

The term unit dosage form refers to physically discrete units suitable as unitary dosages, each unit containing a predetermined quantity of active material calculated to produce the desired therapeutic effect in association with the required pharmaceutical diluent, carrier or vehicle. The specifications for the unit dosage forms of this invention are dictated by and are directly dependent on (a) the unique characteristic of the active material and the particular therapeutic effect to be achieved, and (b) the limitations inherent in the art of compounding such an active material for therapeutic use, as disclosed in detail in this specification, these being features of the present invention.

The invention will be described in greater detail in conjunction with the following specific examples.

EXAMPLE 1

3-(p-Chlorophenyl)-2,3,6,7,8,9-hexadhydro-5H-thiazolo[3,2-a][1,3]diazocin-3-ol, hydrobromide A mixture of 100 g. of 1,5-diaminopentane in 800 ml. of methanol is stirred as 76 g. (60 ml.) of carbon disulfide are added dropwise over one hour while the temperature is maintained at about 30° C. The mixture is allowed to stand 2 hours at room temperature, then is cooled in an ice bath and the solvent is decanted. The residue is mixed with 2 liters of water, stirred at reflux for one hour, treated with charcoal, clarified and then cooled at 4° C., giving 48 g. of hexahydro-1,3-diazocine-2(1H)-thione.

A 2.16 g. portion of hexahydro-1,3-diazocine-2(1H)-thione is dissolved in 800 ml. of hot acetone and then clarified. The clear solution is stirred as 3.5 g. of p-chlorophenacyl bromide are added. The solution is stirred for 20 hours and the solid is collected, washed with 200 ml. of acetone and dried in vacuo, giving 3.3 g. of the desired product, m.p. 201°-202° C. (dec.).

EXAMPLE 2

2,3,6,7,8,9-Hexahydro-2,3-diphenyl-5H-thiazolo-[3,2-a][1,3]diazocin-3-ol, hydrobromide A 2.16 g. portion of hexahydro-1,3-diazocine-2(1H)-thione is dissolved in 800 ml. of hot acetone. The solution is clarified and then stirred as 4.2 g. of 2-bromo-2-phenylacetophenone in 50 ml. of acetone is added. The solution is stirred at room temperature for 7 hours, then the solid is collected, washed with 200 ml. of acetone and dried in vacuo at 60° C., giving 5.1 g. of the desired product, m.p. 211°-213° C. (dec.).

EXAMPLE 3

3-(2-Chloro-5-trifluoromethylphenyl)-2,3,6,7,8,9-hexahydro-5H-thiazolo[3,2-a][1,3]diazocin-3-ol, hydrobromide A 9.0 g. portion of 2-chloro-5-trifluoromethyl acetophenone is dissolved in 150 ml. of dichloromethane. This solution is stirred as a solution of 6.0 g. of bromine in 50 ml. of dichloromethane is added dropwise. A 100 mg. portion of m-chloroperbenzoic acid is added and the mixture is stirred for 2 days. The solution is taken to dryness in vacuo, leaving an oil. The oil is dissolved in 100 ml. of acetone and filtered, giving an acetone solution of 2-bromo-2'-chloro-5'-trifluoromethyl acetophenone.

A suspension of 5.38 g. of hexahydro-1,3-diazocine-2(1H)-thione in 500 ml. of acetone is heated, stirred and then filtered. A 1.85 g. portion of the collected solid is dissolved in 500 ml. of acetone and to this stirred solution is added 34 ml. of the above acetone solution of the 2-bromo ketone. The mixture is stirred for 18 hours, concentrated to about 250 ml. and allowed to stand. The solid is collected, washed with acetone and air dried, giving 2.36 g. of the desired product as light tan crystals, m.p. 208°-211° C. (dec.).

EXAMPLE 4

3-(2,3,4-Trichlorophenyl)-2,3,6,7,8,9-hexahydro-5H-thiazolo[3,2-a][1,3]diazocin-3-ol, hydrobromide A 9.0 g. portion of 2',3',4'-trichloroacetophenone is dissolved in 150 ml. of dichloromethane. A 100 mg. portion of m-chloroperbenzoic acid is added and the solution is stirred as a mixture of 6.0 g. of bromine in 50 ml. of dichloromethane is added dropwise. The mixture is stirred for 12 hours, then refluxed for 5 hours and evaporated in vacuo to an oil. This oil is dissolved in 100 ml. of acetone, providing an acetone solution of 2-bromo-2',3',4-trichloroacetophenone. A 50 ml. portion of this acetone solution is added to a stirred, clarified solution of 3.0 g. of hexahydro-1,3-diazocine-2(1H)-thione in 500 ml. of acetone. The mixture is stirred for 18 hours, the solid is collected, washed with 100 ml. of acetone and dried in vacuo, giving 2.2 g. of the desired product, m.p. 224°-225° C. (dec.).

EXAMPLE 5

3-(p-Chlorophenyl)-2-methyl-2,3,6,7,8,9-hexahydro-5H-thiazolo[3,2-a][1,3]diazocin-3-ol, hydrobromide A 6.6 g. portion of p-chloropropiophenone is dissolved in 150 ml. of dichloromethane and 100 mg. of m-chlorobenzoic acid are added. The solution is stirred as a mixture of 6.0 g. of bromine in 50 ml. of dichloromethane is added dropwise. The solution is stirred for 2 hours, taken to dryness in vacuo and the oil is dissolved in 100 ml. of acetone and clarified, providing an acetone solution of 2-bromo-4'-chloropropiophenone. A 50 ml. portion of this acetone solution is added to a stirred solution of 3.0 g. of hexahydro-1,3-diazocine-2(1H)-thione in 500 ml. of acetone. The mixture is stirred for 18 hours, the solid is collected, washed with 100 ml. of acetone and dried in vacuo, giving 1.6 g. of the desired product, m.p. 212°-213° C. (dec.).

EXAMPLE 6

2-Phenyl-3-(2-thienyl)-2,3,6,7,8,9-hexahydro-5H-thiazolo[3,2-a][1,3]diazocin-3-ol, hydrochloride A mixture of 11.2 g. (9.2 ml.) of thiophene-2-carboxaldehyde, 10.6 g. (10.1 ml.) of benzaldehyde and 8.0 g. of potassium cyanide in 100 ml. of 65% ethanol is heated at 100° C. for 2 hours. The mixture is then diluted with 125 ml. of 50% ethanol and chilled. The solid is collected, washed with 25 ml. of 50% ethanol and recrystallized from absolute ethanol with chilling for 2 hours. These crystals are collected, washed with ice cold absolute ethanol, air dried and finally recrystallized from 50 ml. of absolute ethanol and dried giving 5.41 g. of 2-thienyl-α-hydroxybenzyl ketone.

To a stirred suspension of 2.63 g. of the above ketone in 25 ml. of toluene containing 2.63 g. of triethylamine, is added dropwise a solution of 1.60 g. (1.08 ml.) of methanesulfonyl chloride in 25 ml. of toluene. The mixture is allowed to stand overnight, the solid is collected, washed with water, dried and recrystallized from ethanol, giving 2.34 g. of 2-thienyl(α-methanesulfonyloxybenzyl)-ketone.

A mixture of 1.28 g. of hexahydro-1,3-diazocine-2(1H)-thione and 700 ml. of acetone is heated to a boil and then filtered. To this solution is added a solution of 2.34 g. of 2-thienyl(α-methanesulfonyloxybenzyl)ketone in 50 ml. of acetone. The mixture is allowed to stand overnight and is then filtered and concentrated in vacuo to about 150 ml. This concentrate is further evaporated to near dryness, dissolved in 60 ml. of water, decanted from the solids and made alkaline with ammonium hydroxide. The resulting solid is collected, washed with water, dried and dissolved in 50 ml. of acetone. This solution is filtered and 10 ml. of 3.55 N ethanolic hydrogen chloride are added. The mixture is filtered clear of solids and seeded to produce crystals of the desired product (1.15 g.), m.p. 201°–203° C. (dec.).

EXAMPLE 7

2-Methyl-3-phenyl-2,3,6,7,8,9-hexahydro-5H-thiazolo[3,2-a][1,3]diazocin-3-ol, hydrobromide A mixture of 1.44 g. of hexahydro-1,3-diazocine-2(1H)-thione and 500 ml. of acetone is heated to produce solution. A 2.13 g. portion of 2-bromopropiophenone is added and the mixture is allowed to stand overnight. The solid is collected, washed with acetone and dried, giving 2.53 g. of the desired product, m.p. 191°–193° C. (dec.).

We claim:

1. A compound of the formula:

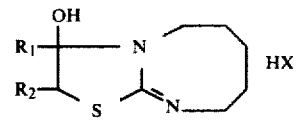

wherein $R_1$ is phenyl, p-chlorophenyl, 2,3,4-trichlorophenyl, 2-chloro-5-trifluoromethylphenyl or 2-thienyl; $R_2$ is hydrogen, methyl or phenyl; and X is chloro or bromo.

2. The compound according to claim 1 wherein $R_1$ is p-chlorophenyl, $R_2$ is hydrogen, and X is bromo: 3-(p-chlorophenyl)-2,3,6,7,8,9-hexahydro-5H-thiazolo[3,2-a][1,3]diazocin-3-ol hydrobromide.

3. The compound according to claim 1 wherein $R_1$ and $R_2$ are both phenyl, and X is bromo: 2,3-diphenyl-2,3,6,7,8,9-hexahydro-5H-thiazolo[3,2-a][1,3]diazocin-3-ol hydrobromide.

4. The compound according to claim 1 wherein $R_1$ is 2-chloro-5-trifluoromethylphenyl, $R_2$ is hydrogen, and X is bromo: 3-(2-chloro-5-trifluoromethylphenyl)-2,3,6,7,8,9-hexahydro-5H-thiazolo[3,2-a][1,3]diazocin-3-ol hydrobromide.

5. The compound according to claim 1 wherein $R_1$ is 2,3,4-trichlorophenyl, $R_2$ is hydrogen, and X is bromo: 3-(2,3,4-trichlorophenyl)-2,3,6,7,8,9-hexahydro-5H-thioazolo[3,2-a][1,3]diazocin-3-ol hydrobromide.

6. The compound according to claim 1 wherein $R_1$ is p-chlorophenyl, $R_2$ is methyl, and X is bromo: 2-methyl-3-(p-chlorophenyl)-2,3,6,7,8,9-hexahydro-5H-thiazolo[3,2-a][1,3]diazocin-3-ol hydrobromide.

7. The compound according to claim 1 wherein $R_1$ is 2-thienyl, $R_2$ is phenyl, and X is chloro: 2-phenyl-3-(2-thienyl)-2,3,6,7,8,9-hexahydro-5H-thiazolo[3,2-a][1,3]diazocin-3-ol hydrochloride.

8. The compound according to claim 1 wherein $R_1$ is phenyl, $R_2$ is methyl, and X is bromo: 2-methyl-3-phenyl-2,3,6,7,8,9-hexahydro-5H-thiazolo[3,2-a][1,3]diazocin-3-ol hydrobromide.